United States Patent
Park et al.

(10) Patent No.: US 9,849,323 B2
(45) Date of Patent: Dec. 26, 2017

(54) DECONTAMINATION AND STERILIZATION DEVICE WITH FLEXIBLE ENCLOSING COVER USING PLASMA AND REACTIVE GAS

(71) Applicant: AGENCY FOR DEFENSE DEVELOPMENT, Daejeon (KR)

(72) Inventors: Myung-Kyu Park, Daejeon (KR); Hee-Soo Jung, Sejong-si (KR)

(73) Assignee: AGENCY FOR DEFENSE DEVELOPMENT, Daejeon (KR)

( * ) Notice: Subject to any disclaimer, the term of this patent is extended or adjusted under 35 U.S.C. 154(b) by 0 days.

(21) Appl. No.: 15/378,527

(22) Filed: Dec. 14, 2016

(65) Prior Publication Data

US 2017/0182342 A1   Jun. 29, 2017

(30) Foreign Application Priority Data

Dec. 24, 2015   (KR) .......................... 10-2015-0186193

(51) Int. Cl.
*A61L 12/14*    (2006.01)
*A62D 3/19*    (2007.01)
(Continued)

(52) U.S. Cl.
CPC .................. *A62D 3/19* (2013.01); *A61L 2/14* (2013.01); *B01J 19/088* (2013.01);
(Continued)

(58) Field of Classification Search
CPC ..... A62D 3/19; A62D 2101/02; B01J 19/088; B01J 2219/0809; B01J 2219/0826;
(Continued)

(56) References Cited

U.S. PATENT DOCUMENTS

| | | | |
|---|---|---|---|
| 2010/0247403 A1* | 9/2010 | Hancock | A61L 2/14 422/186.29 |
| 2012/0063966 A1* | 3/2012 | Liao | A61L 2/14 422/186 |
| 2015/0179411 A1* | 6/2015 | Laux | H01J 37/32568 423/659 |

FOREIGN PATENT DOCUMENTS

| | | |
|---|---|---|
| JP | 2014-505553 A | 3/2014 |
| KR | 10-1041026 B1 | 6/2011 |

(Continued)

*Primary Examiner* — Xiuyu Tai
(74) *Attorney, Agent, or Firm* — LRK Patent Law Firm

(57) ABSTRACT

A device for removing toxic or harmful materials from an inside sealed by a sealed-type flexible enclosing cover, wherein the contaminated surface of the subject of decontamination is covered with the enclosing cover and a reactive gas is introduced thereto, and particularly to a decontamination and sterilization device, wherein a plasma generator is fixed to a enclosing cover and a plasma gas containing an active radical generated from the plasma generator is introduced to the inside sealed by the enclosing cover together with a reactive gas having a hydroxyl group such as hydrogen peroxide ($H_2O_2$), water ($H_2O$), or an alcohol ($C_nH_{2n+1}OH$) to thus increase the production of a reactive radical, whereby the plasma and the reactive gas are intensively applied to the inside sealed by the enclosing cover, thus increasing the contact with contaminants and realizing more efficient decontamination.

14 Claims, 16 Drawing Sheets

(51) Int. Cl.
*A61L 2/14* (2006.01)
*B01J 19/08* (2006.01)
*H01J 37/32* (2006.01)
*A62D 101/02* (2007.01)

(52) U.S. Cl.
CPC .... *H01J 37/3244* (2013.01); *H01J 37/32348* (2013.01); *H01J 37/32541* (2013.01); *H01J 37/32596* (2013.01); *A61L 2202/11* (2013.01); *A62D 2101/02* (2013.01); *B01J 2219/083* (2013.01); *B01J 2219/0809* (2013.01); *B01J 2219/0826* (2013.01); *B01J 2219/0841* (2013.01); *B01J 2219/0879* (2013.01); *B01J 2219/0894* (2013.01)

(58) Field of Classification Search
CPC .......... B01J 2219/083; B01J 2219/0841; B01J 2219/0879; B01J 2219/0894; H01J 37/32348; H01J 37/3244; H01J 37/32541; H01J 37/32596; A61L 2/14; A61L 2202/11
See application file for complete search history.

(56) References Cited

FOREIGN PATENT DOCUMENTS

| | | |
|---|---|---|
| KR | 10-1055664 B1 | 8/2011 |
| KR | 2015-0107922 A | 9/2015 |
| KR | 10-1573231 B1 | 12/2015 |

\* cited by examiner

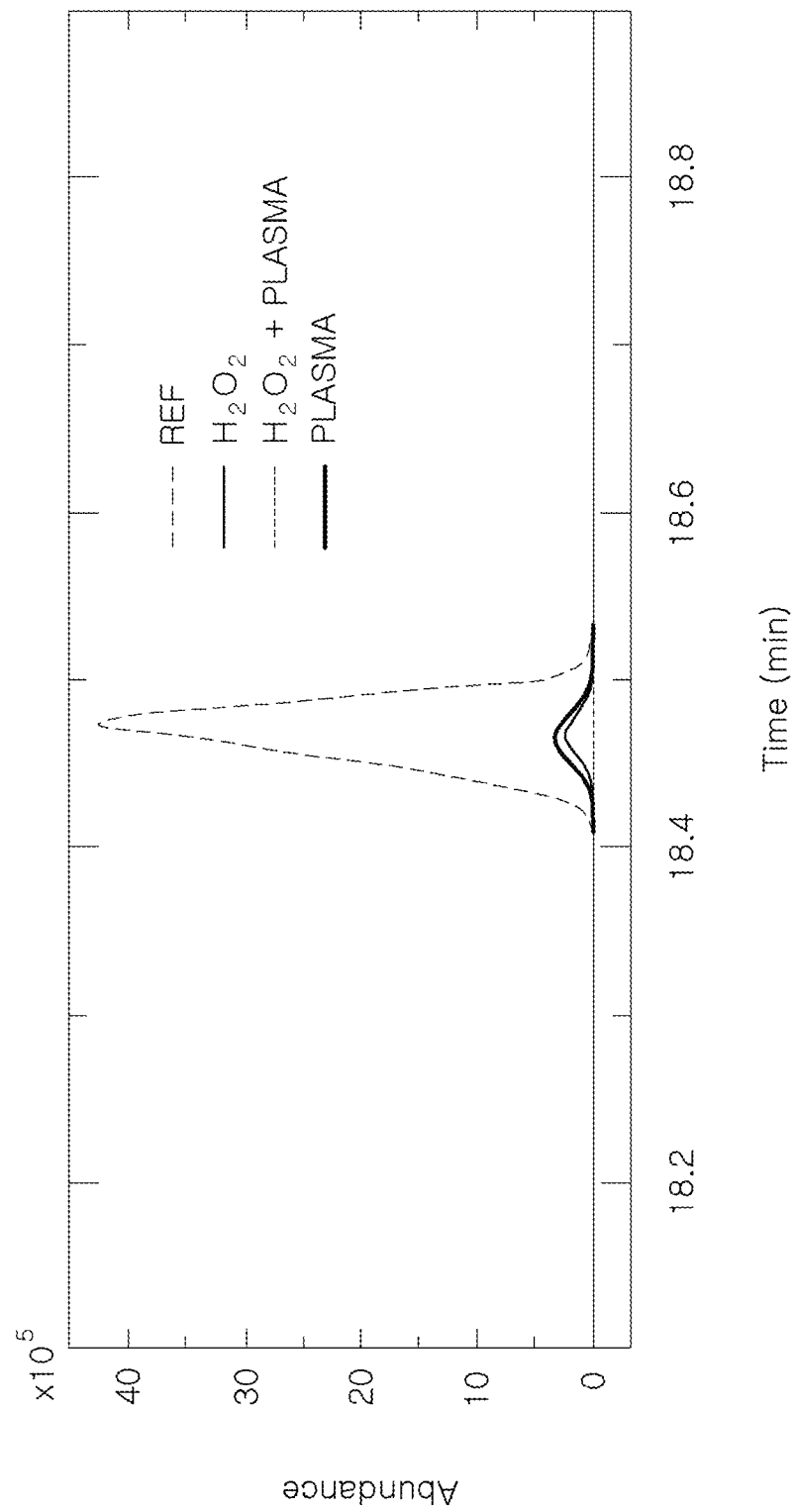

DECONTAMINATION AND STERILIZATION DEVICE WITH FLEXIBLE ENCLOSING COVER USING PLASMA AND REACTIVE GAS

CROSS REFERENCE TO RELATED APPLICATION(S)

The present application claims priority to Korean Patent Application No. 10-2015-0186193, filed Dec. 24, 2015, the entire content of which is incorporated herein by reference.

BACKGROUND OF THE INVENTION

1. Technical Field

The present invention relates to a device for efficiently removing contaminants from an inside sealed by a enclosing cover, in which the contaminated surface of the subject of decontamination is covered with the enclosing cover and a reactive gas is introduced thereto, and more particularly to a decontamination and sterilization device for purifying the contaminated surface covered with a sealed-type flexible enclosing cover, in which a plasma generator is fixed to the flexible enclosing cover and plasma and a reactive gas are intensively introduced to the inside sealed by the enclosing cover.

2. Description of Related Art

In nuclear, biological and chemical (NBC) contamination situations or battlefields, when chemical and biological agents are sprayed, the surface of vehicles or equipment may be contaminated, thus being highly toxic to human bodies. In this case, urgent decontamination processing is required. Currently, decontamination is mainly performed using water or water-soluble antidotes. However, water or water-soluble antidotes containing chemical components having high oxidizing power are difficult to use for decontamination of electronic equipment sensitive to chemicals, indoor decontamination, or decontamination of the surface of equipment having porous or complicated surface structures.

With the goal of solving problems with such water-soluble antidotes, thorough research is ongoing. In this regard, typical examples of decontamination techniques may include decontamination of the contaminated surface of a solid using atmospheric pressure plasma, surface decontamination using an oxidizing gas such as hydrogen peroxide, etc. In particular, a plasma decontamination device is useful, in which plasma is, generated by high-voltage electrodes, and the produced reactive radicals or reactive chemicals are brought into contact with contaminants to thus induce chemical reactions and decompose contaminants.

Specifically, a plasma decontamination process is carried out in a manner such that hydrogen peroxide, water vapor, helium, and argon are introduced into a plasma generation part, and alternating current (AC) ranging from hundreds of volts (V) to tens of kilovolts (KV) between two electrodes is applied to such reactive gases under atmospheric pressure, whereby atmospheric pressure plasma is generated through a plasma discharge phenomenon. As such, electrons or ions in the plasma come into contact with air or gas, especially water, hydrogen peroxide, alcohol, or acetone, in the discharge zone and are thus ionized and decomposed, thereby forming active radicals having high oxidizing capability. The radicals thus formed are very reactive, and thus a variety of bacteria and chemicals may be effectively removed within a time range from several seconds to several minutes from the contaminated surface.

The properties of the plasma thus generated may vary depending on the magnitude of the voltage applied to the electrodes, the applied frequency, and conditions for generating plasma, and may also considerably depend on the electron density produced between electrodes, plasma temperature, and required electric power. Hence, plasma has to be generated and applied under plasma discharge conditions suitable for plasma requirements.

Typically, a plasma electrode device for decontaminating the surface of vehicles, equipment or sensitive and complicated electronic instruments has to operate at a low temperature of 100° C. or less so that the subject of decontamination is not thermally damaged when decontaminated. To this end, a glow discharge plasma device that discharges plasma at ones of kHz, a dielectric barrier plasma device, or a plasma jet is mainly useful. Such a plasma device has relative low contaminant decomposition efficiency per unit time and thus requires a long period of contact with the contaminant. As another plasma device, when plasma having a high frequency of MHz or GHz is used, the contaminant decomposition efficiency is high, but high power, an incidental matching system, a shield, a waveguide and the like are additionally required.

For the decontamination and sterilization of materials contaminated with chemical or biological agents, thorough research into plasma jets configured to emit the discharged plasma in the form of a jet has been carried out.

However, when a single plasma jet is used, the contact area of the contaminated surface of the subject of decontamination is narrow, active radicals are very unstable and thus have very short retention time in air, and high-purity helium or argon gas has to be additionally fed to increase plasma electron density in order to form conditions favorable for the generation of plasma, undesirably making it difficult to move the device and feed gas necessary therefor. Therefore, limitations are imposed on the use of the plasma decontamination device in a battlefield or outdoors.

Also, in the case where only a plasma jet is utilized on the contaminated surface of equipment exposed to air, it is difficult to bring plasma into direct contact with the contaminated surface or to continuously generate a very large amount of plasma, attributable to the flow of air, the temperature of air, and diffusion effects, thus making it difficult to maintain the produced reactive radicals at high concentration. Therefore, there are spatial and financial limitations on the rapid removal of surface contaminants to a high efficiency of 99.9% or more.

SUMMARY OF THE INVENTION

Accordingly, the present invention has been made keeping in mind the above problems encountered in the related art, and the present invention is intended to provide a decontamination and sterilization device configured such that a reactive decontamination gas generator is attached to a enclosing cover for covering and sealing contaminated equipment, in which the reactive decontamination gas generator makes it possible to mix and spray both a plasma gas and a reactive gas for producing a large amount of a radical having high reactivity onto the surface of contaminated equipment, especially a structure or equipment contaminated with a chemical agent or a biological agent.

The present invention is intended to provide a decontamination and sterilization device, in which plasma generated from a reactive decontamination gas generator is continuously sprayed to an inside sealed by a enclosing cover so that the concentration of a reactive radical or a reactive gas within the inside sealed by the enclosing cover is increased, thereby increasing the contact time of the reactive radical with the contaminated surface and the concentration thereof, as a consequence of which the decontamination efficiency may be increased.

The present invention provides a decontamination and sterilization device, comprising a enclosing cover, which is composed of a non-conductive flexible material and is configured to cover and seal a portion of the surface of the subject of decontamination contaminated with a chemical agent or a biological agent, and reactive decontamination gas generators, which are spaced apart from each other at a predetermined distance on the enclosing cover and are configured such that a decontamination gas, namely a plasma gas and a reactive gas for producing an active radical are simultaneously or independently sprayed to the inside sealed by the enclosing cover, in which each of the reactive decontamination gas generators includes an electrode structure configured such that a metal tube-type internal electrode, which receives external air via a first inflow path formed at one end thereof so as to generate plasma, is housed in the center of an external electrode.

In the electrode structure, the internal electrode may communicate with a second inflow path into which the reactive gas flows, so that the reactive gas is fed into the internal electrode in which plasma is not generated, whereby the reactive gas is sprayed together with the plasma gas at the center of the reactive decontamination gas generator to thus facilitate the mixing of the plasma gas and the reactive gas.

In the electrode structure, the internal electrode is provided in the form of a metal tube, and may have a cylindrical shape, or a polygonal prism shape having a rectangular cross-sectional shape or a hexagonal cross-sectional shape.

The electrode structure may include a plasma generation part provided in an empty space between the internal electrode and the external electrode so as to generate a plasma gas, and the plasma generation part may further include spherical dielectrics using at least one dielectric material having a high dielectric constant selected from among $BaTiO_3$, $TiO_2$, glass and ceramic, in order to increase the plasma electron density.

Alternatively, a cylindrical dielectric may, be formed around the inner surface of the external electrode so as to come into contact therewith.

Alternatively, the electrode structure may be configured such that one or more internal electrodes and one or more external electrodes tare alternately arranged, and the electrode structure may be configured such that an insulation material for preventing, current leakage may be formed around the outer surface of the external, electrode, which is located at the outermost position.

The electrode structure may further include multiple needle-shaped electrodes formed at positions in which the internal electrodes and the external electrodes are disposed to face each other.

The electrode structure of the invention is described in detail through the following embodiments. The electrode structure thus disclosed is preferable, but the present invention is not limited thereto. The electrode structure of the invention may be composed of a glow discharge device, an arc discharge device, or a dielectric barrier plasma discharge device.

The enclosing cover of the invention includes an opening/closing-type fixing jig (not shown) for fixing each of the reactive decontamination gas generators. When the reactive decontamination gas generator is not attached, the opening/closing-type fixing jig is opened to realize air circulation, such as the outflow of contaminated air or inflow of external air, and may be closed, as necessary.

The opening/closing-type fixing jig enables one end of the reactive decontamination gas generator to be removably attached to the enclosing cover in a screw-fastening manner or a one-touch coupling manner. The present invention is not limited to the above connection process, but a variety of connection processes, which may be easily performed by those skilled in the art, may be applied so as to achieve removable attachment.

The opening/closing-type fixing jig may be further provided with a hollow spacing panel that functions to prevent the interruption of emission of the decontamination gas due to the contact of the spray outlet of the reactive decontamination gas generator with the surface of the subject of decontamination to thus facilitate the flow of decontamination gas or air in the inside sealed by the enclosing cover and that also functions to space the enclosing cover, having the reactive decontamination gas generator, apart from the surface of the subject of decontamination in order to prevent current leakage between the electrodes and the surface of the subject of decontamination.

Meanwhile, one side of the first inflow path may be provided with a humidity controller for controlling the relative humidity of the external air that is fed into the reactive decontamination gas generator, and the enclosing cover may further include an air ventilation fan for circulating air therein.

The enclosing cover may further include a fixing member at an edge thereof so as to prevent it from being blown away by wind, so that it may be fixed to or kept in close contact with the surface of the subject of decontamination.

Examples of the material for the enclosing cover may include, but are not limited to, fabric, leather, vinyl and polymers, and not only non-conductive flexible materials having chemical resistance but also impermeable materials for preventing the infiltration of external air and leakage of the decontamination gas via the enclosing cover may be used.

Fed into the reactive decontamination gas generator of the invention, the reactive gas may be a material having a hydroxyl group, such as hydrogen peroxide ($H_2O_2$), water ($H_2O$) or alcohol ($C_nH_{2n+1}OH$, wherein n is an integer of 1 to 10). Here, any liquid or gas may be used without particular limitation, so long as it is able to produce a large amount of active radical such as ozone ($O_3$), $.O^-$, or $OH^-$ when reacting with plasma. Preferably useful is at least one selected from among hydrogen peroxide ($H_2O_2$), water vapor ($H_2O$), helium, argon, acetone, oxygen, compressive air, and alcohol ($C_nH_{2+n}OH$).

In addition, the decontamination and sterilization device as described above may be used as a structural unit for providing an expandable decontamination and sterilization device assembly in a manner such that individual structural units are capable of being repeatedly connected to each other using connectors formed at the edges of individual enclosing covers thereof.

According to the present invention, a decontamination and sterilization device is composed of a flexible enclosing cover and is thus very flexible. Under the condition that the contaminated surface is covered with the enclosing cover and is partially sealed, a plasma gas and a reactive gas are fed so as to perform decontamination, whereby the retention time of the plasma gas and the reactive gas responsible for decontamination on the contaminated surface and the decomposition time of contaminants are prolonged, thus increasing the efficiency of removal of contaminants.

The decontamination and sterilization device of the invention is able to cover the subject of decontamination to thus decontaminate it, regardless of the shape of the subject of decontamination. Also, the decontamination and sterilization device as described above can be used as a structural unit for providing an expandable decontamination and sterilization device assembly in a manner in which individual structural units are repeatedly connected to each other. Accordingly, the decontamination and sterilization device of the invention is useful regardless of the size and shape of the subject of decontamination, and regardless of the material constituting the subject of decontamination, such as a porous material or liquid-phase contaminated surface, which is typically difficult to decontaminate.

In, the decontamination and sterilization device of the invention, a radical such as ozone ($O_3$), $.O^-$, or $OH^-$, generated during operation of the plasma electrode, has very high reactivity and can thus cause a chemical reaction with the contaminant on the surface of a solid, thereby removing not only chemical contamination but also biological contamination due to bacteria or viruses. Furthermore, it can be applied to civilian purposes, including the removal of mites from beds or sofas, cleaning of the living environment in everyday life, including military goods, and sanitary treatment.

Also, in the reactive decontamination gas generator of the invention, the internal electrode is used as a reactive gas feed path, and thus the reactive gas can be mixed with a plasma-activating gas at the outlet of the reactive decontamination gas generator, thereby producing a reactive radical at a high concentration and increasing the decomposition performance and decontamination efficiency of contaminants using such a radical.

In the decontamination and sterilization device of the invention, the generation of plasma and the introduction of reactive gas can be simultaneously or separately performed within the inside sealed by the enclosing cover, and the gas introduction sequence can be selected as desired, thus increasing the efficiency of decomposition and decontamination of contaminants.

Moreover, in the decontamination and sterilization device of the invention, a dielectric barrier structure is applied to the plasma generation electrode, thus generating plasma at high electron density, thereby efficiently producing a reactive radical and removing the surface contaminants.

The technical effects of the present invention are not limited to the foregoing, and other effects not mentioned herein will be able to be clearly understood by those skilled in the art from the following description.

BRIEF DESCRIPTION OF THE DRAWINGS

FIG. 16 is a graph showing the decontamination efficiency in the test of the present invention.

DESCRIPTION OF THE SPECIFIC EMBODIMENTS

As used herein, it will be understood that the terms "comprise", "include", "have", etc., when used in this specification, specify the presence of stated features, numerals, steps, operations, elements, parts, and/or combinations thereof, but do not, preclude the presence or addition of one or more other features, numerals, steps, operations, elements, parts, and/or combinations thereof.

Hereinafter, a detailed description will be given of embodiments of the present invention taken in conjunction with the accompanying drawings. Such embodiments may be realized in different forms by those skilled in the art, and are not construed as limiting the present invention.

Figure 1:
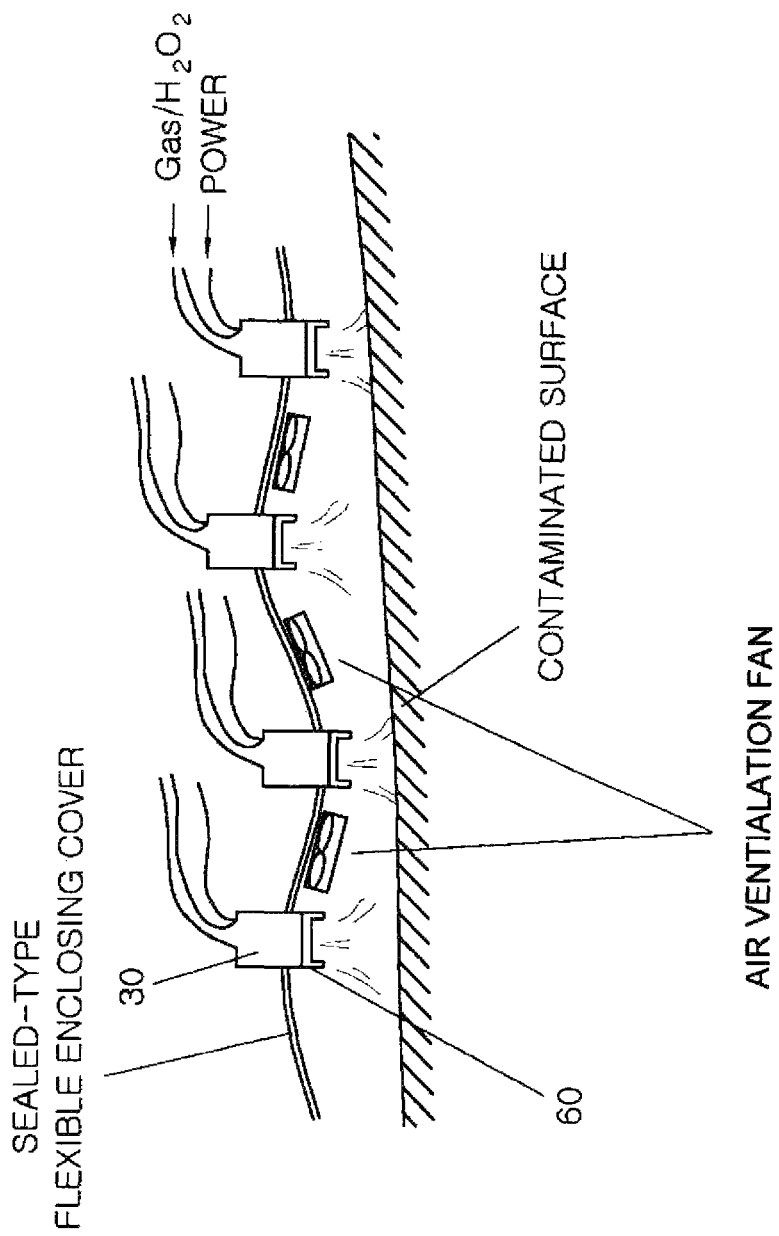
FIG. 1 is a cross-sectional view showing a decontamination and sterilization device according to an embodiment of the present invention.
Figure 2:
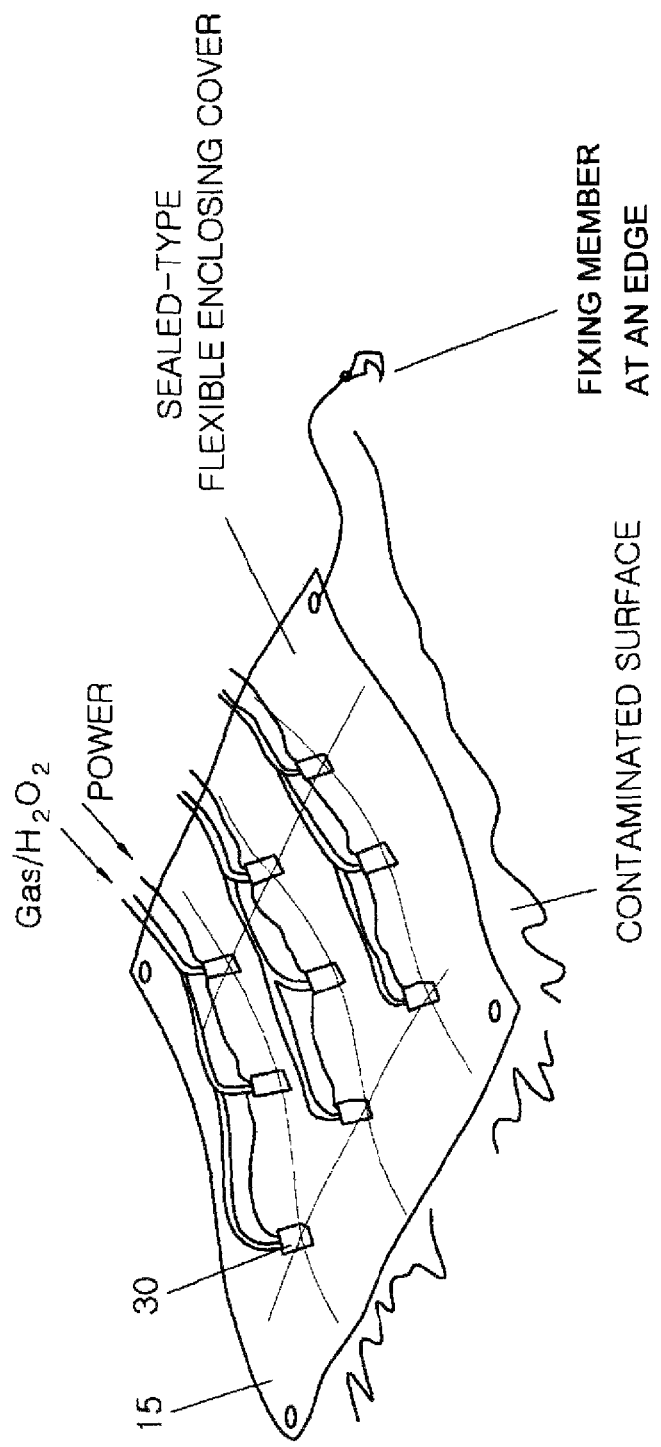
FIG. 2 is a perspective view showing the decontamination and sterilization device according to an embodiment of the present invention.

FIGS. 1 and 2 show the decontamination and sterilization device 100 according, to an embodiment of the present invention. As shown in FIGS. 1 and 2, in order to overcome limitations on decontamination efficiency when using only plasma, the decontamination and sterilization device of the invention is configured such that reactive decontamination gas generators 30 for simultaneously spraying both a plasma gas and a reactive gas are removably attached to an impermeable flexible enclosing cover 15 so as to be spaced apart from each other by a predetermined distance, and an active radical is produced by passing reactive gas, or air through the reactive decontamination gas generators 30 for generating a decontamination gas from the outside of the enclosing cover 15, and is sprayed to the inside sealed by the flexible impermeable sealed-type enclosing cover, whereby the contaminated surface sealed by the enclosing cover may be efficiently decontaminated.

Figure 3:
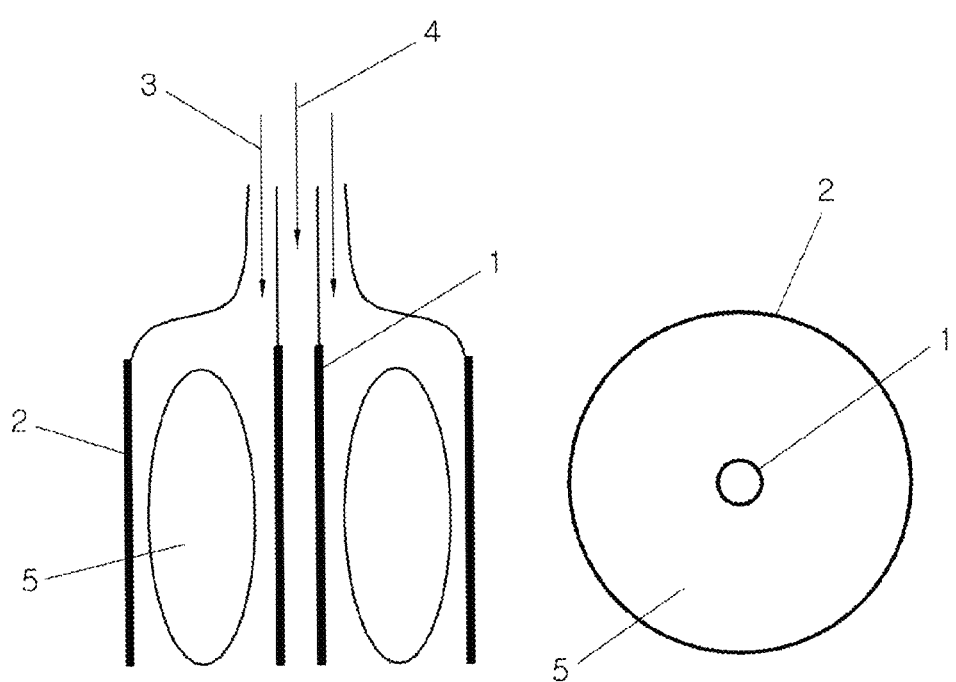
FIG. 3 shows a reactive decontamination gas generator according to an embodiment of the present invention.

FIG. 3 shows the reactive decontamination gas generator 30 according to an embodiment of the present invention.

As shown in FIG. 3, the reactive decontamination gas generator 30 includes an electrode structure 1, 2 having a cylindrical shape, such as that of a pipe or a cylinder, so as to generate plasma. Specifically, the electrode structure 1, 2 includes an internal electrode 1, which is in the form of a metal tube and receives external air via the first inflow path 16 formed at one end thereof to generate plasma, and an external electrode 2, which is disposed concentrically around the internal electrode 1, and a plasma generation part 5 for generating a plasma gas is provided in an empty space between the internal electrode 1 and the external electrode 2.

Hydrogen peroxide ($H_2O_2$), which is an example of a reactive gas, is very unstable, and is converted into water and oxygen when allowed to stand in an ambient atmosphere. When it is converted into a vapor and comes into contact with another material, it may be mainly used as an oxidizing agent or a bleaching agent due to its strong oxidizing power. When energy such as plasma is applied to hydrogen peroxide, hydrogen peroxide is easily decomposed and thus a reactive radical such as OH— or the like may be produced. Using the properties of the hydrogen peroxide, when hydrogen peroxide is mixed with a plasma gas upon generating plasma, the formation of a reactive radical occurs during the decomposition of the reactive gas, thus promoting the degradation of contaminants.

In the electrode structure 1, 2 of the invention, the internal electrode 1 may communicate with the second inflow path 17, into which the reactive gas flows, so that, the reactive gas is introduced into the internal electrode 1, in which plasma is not generated. Thereby, together with the generation of plasma, the reactive gas may be efficiently mixed with the generated plasma in the electrode structure 1, 2 and then sprayed onto the contaminated surface, thus enabling efficient decontamination of the contaminated surface.

Figure 4:
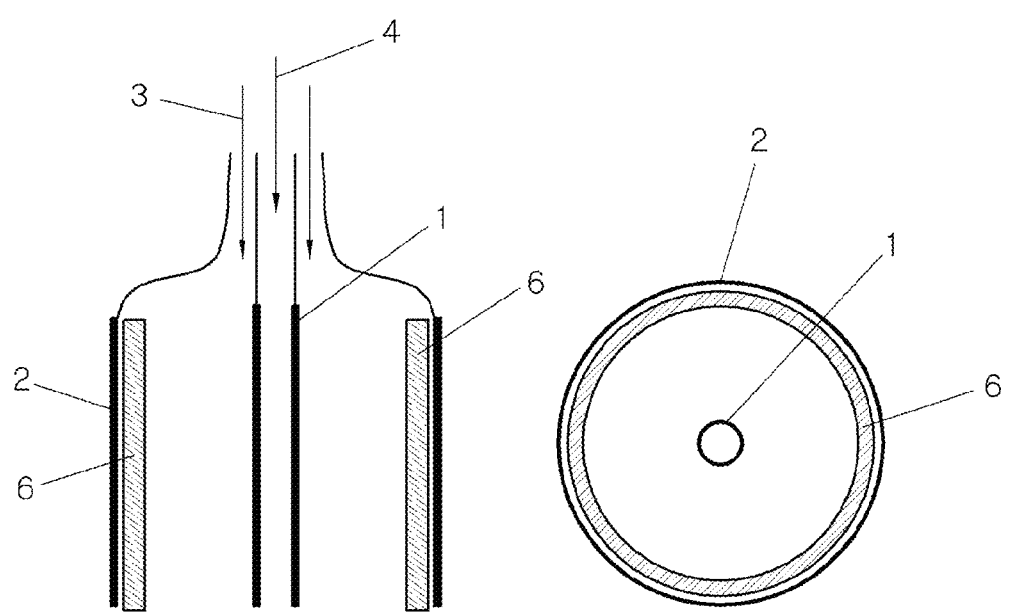
FIG. 4 schematically shows the reactive decontamination gas generator of FIG. 3 provided with a cylindrical dielectric material.
Figure 5:
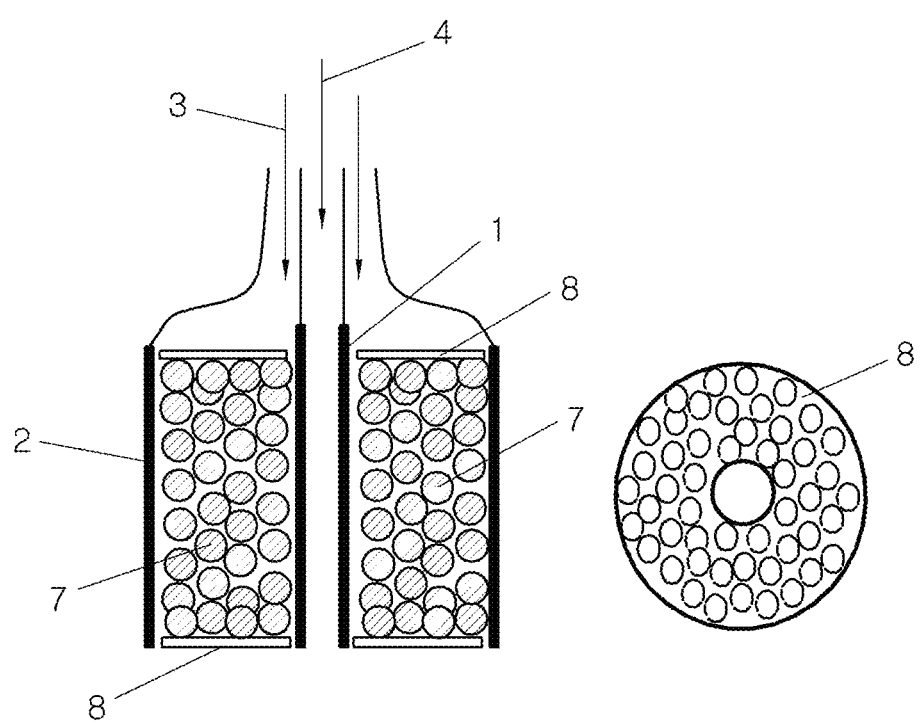
FIG. 5 schematically shows the reactive decontamination gas generator of FIG. 3 provided with a bead-shaped dielectric material.

FIGS. 4 and 5 show the electrode structures 1, 2 of the reactive decontamination gas generators, which include dielectrics having a high dielectric constant, so that the plasma generation efficiency, namely the plasma electron density, is increased.

As illustrated in FIG. 4, a cylindrical dielectric 6 may be formed around the inner surface of the external electrode so as to come into contact therewith, or alternatively, as illustrated in FIG. 5, spherical dielectrics 7 may be loaded in the plasma generation part 5 formed between the internal electrode 1 and the external electrode 2. In the case where the spherical dielectrics 7 are used, non-metal dielectric plugs 8 may be provided at opposite ends of the plasma generation part so that the spherical dielectrics 7 do not escape but may be present only in the plasma generation part depending on the flow of the fluid introduced into the reactive decontamination gas generator.

In the present invention, the dielectrics 6, 7 may include at least one dielectric material selected from among $BaTiO_3$, $TiO_2$, glass and ceramic.

Figure 6:
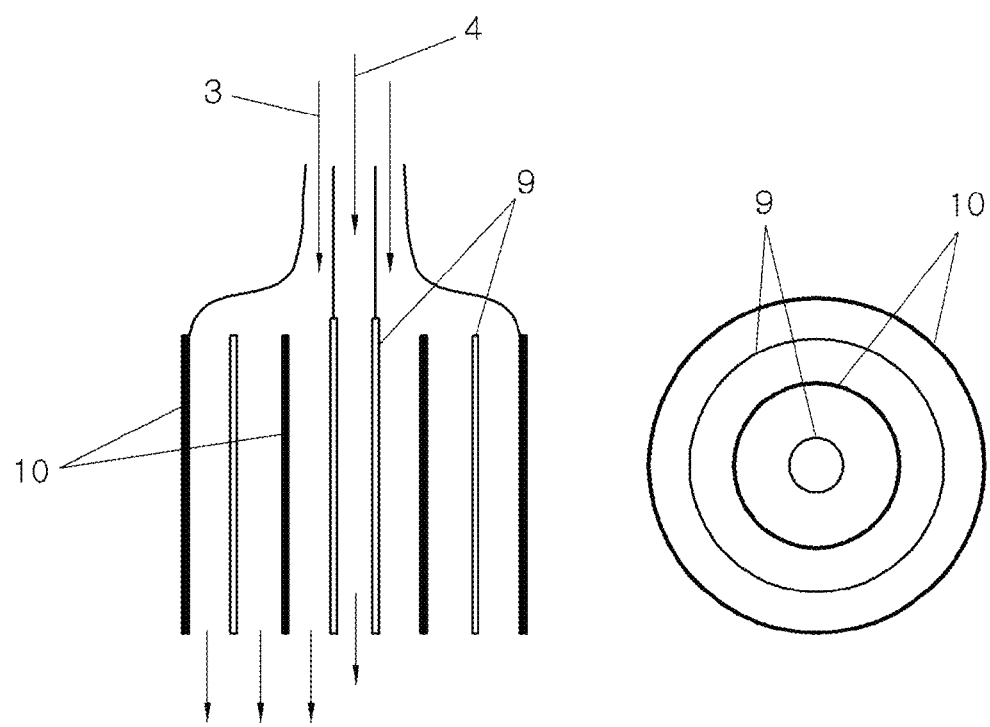
FIG. 6 schematically shows the reactive decontamination gas generator of FIG. 3 in which a multilayered electrode structure is provided to generate plasma.

FIG. 6 shows the reactive decontamination gas generator of the invention, in which a multilayered concentric electrode structure 1, 2 is formed. As shown in FIG. 6, the first electrode structure 9 and the second electrode structure 10 may be configured such that internal electrodes and external electrodes are alternately concentrically arranged. As such, only the internal electrode of the first electrode structure 9, which is located at the innermost, center position, is utilized as the reactive gas path.

FIGS. 7 to 10 show the configurations of the electrode structures 1, 2 of the reactive decontamination gas generators of FIGS. 3 to 6, in which multiple needle-shaped electrodes are formed. As shown in FIGS. 7 to 10, sharp needle-shaped electrodes may be further formed at the positions in which the internal electrodes and the external electrodes are disposed to face each other, thus more effectively generating a plasma gas.

Figure 7:
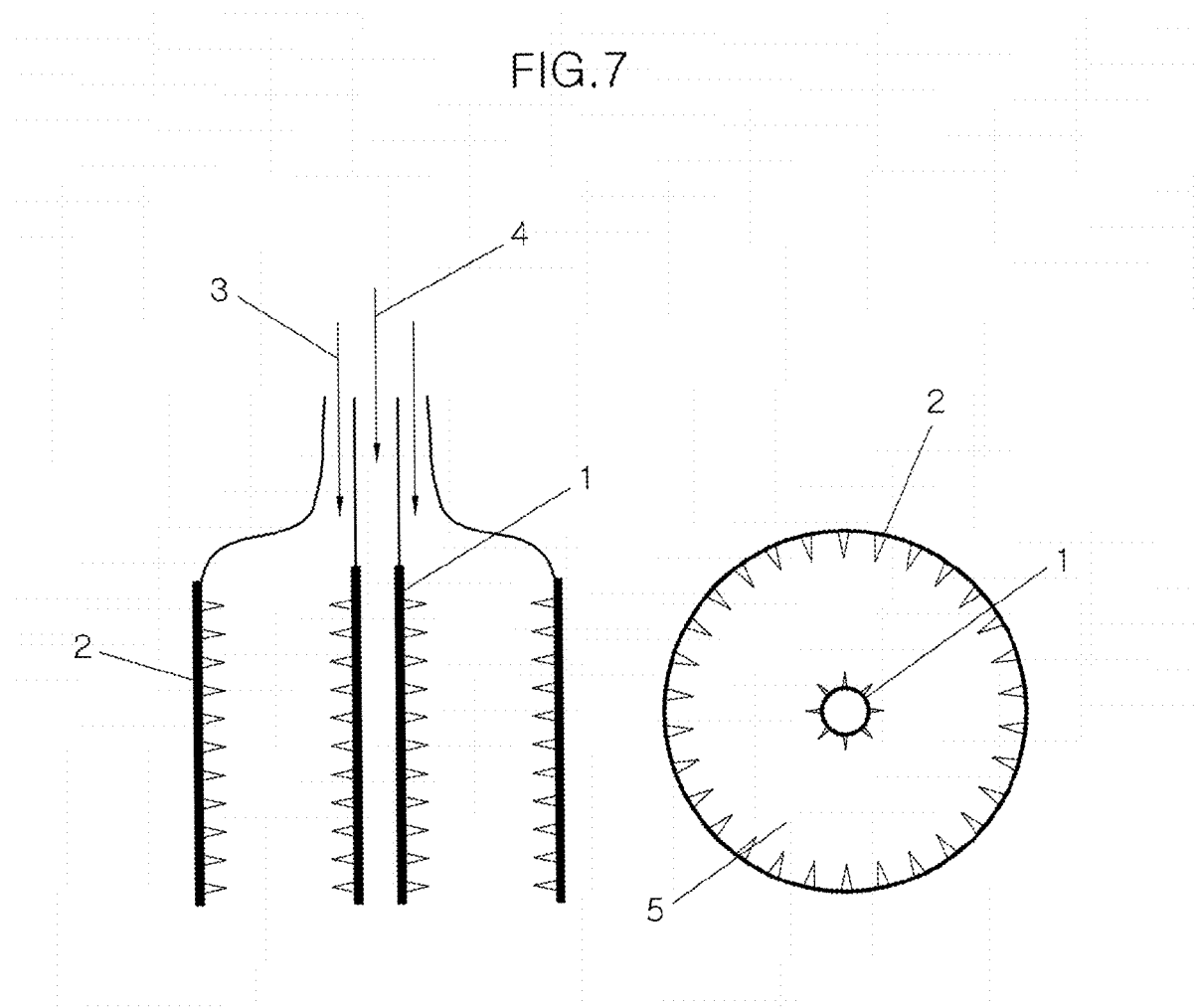
FIG. 7 schematically shows the configuration of the electrode structure provided with multiple needles in the reactive decontamination gas generator of FIG. 3.
Figure 9:
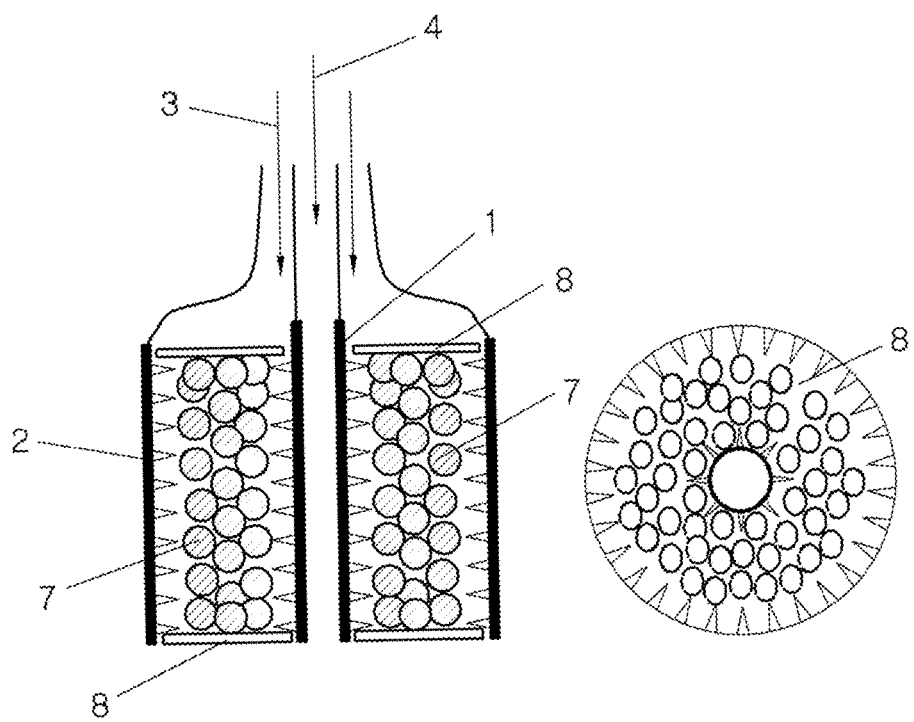
FIG. 9 schematically shows the configuration of the electrode structure provided with multiple needles in the reactive decontamination gas generator of FIG. 5.

As shown in FIGS. 7 and 9, the electrode structure 1, 2 is configured such that needle-shaped electrodes are further provided at the positions in which the internal electrode 1 and the external electrode 2 are disposed to face each other. As shown in FIG. 9, the plasma generation part 5 formed between the needle-shaped electrodes may be filled with the dielectrics 7, as is apparent from FIG. 5.

Figure 8:
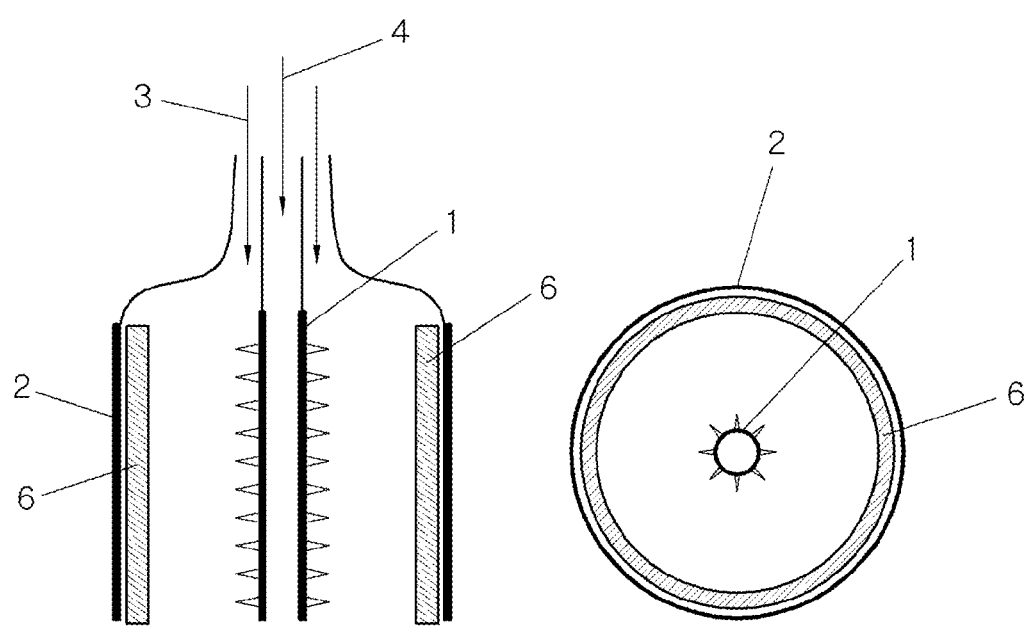
FIG. 8 schematically shows the configuration of the electrode structure provided with multiple needles in the reactive decontamination gas generator of FIG. 4.

In another configuration, as shown in FIG. 8, when a cylindrical dielectric 6 is formed around the inner surface of the external electrode so as to come into contact therewith, needle-shaped electrodes may be provided only on the internal electrode on which the dielectric is not formed.

Figure 10:
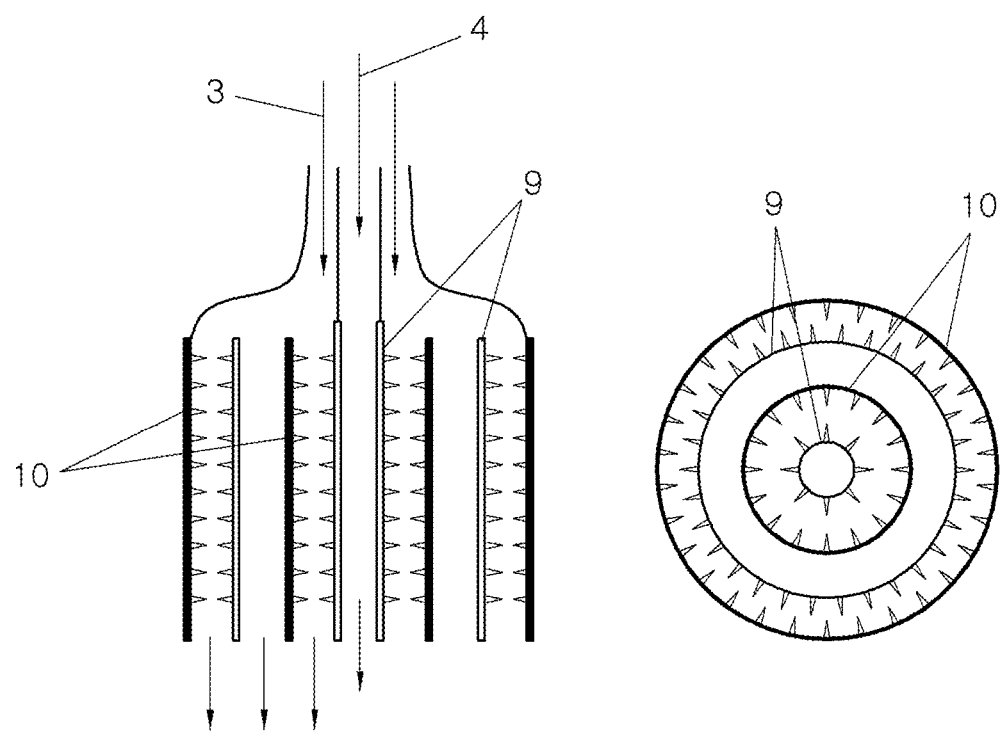
FIG. 10 schematically shows the configuration of the electrode structure provided with multiple needles in the reactive decontamination gas generator of FIG. 6.

In another configuration, as shown in FIG. 10, the electrode structure includes the first electrode structure 9 and the second electrode structure 10, in which the internal electrodes and the external electrodes are alternately concentrically arranged. In this case, in the configuration of the first and second electrode structures, needle-shaped electrodes are further provided at the positions in which the internal electrodes and the external electrodes are disposed to face each other.

Figure 11:
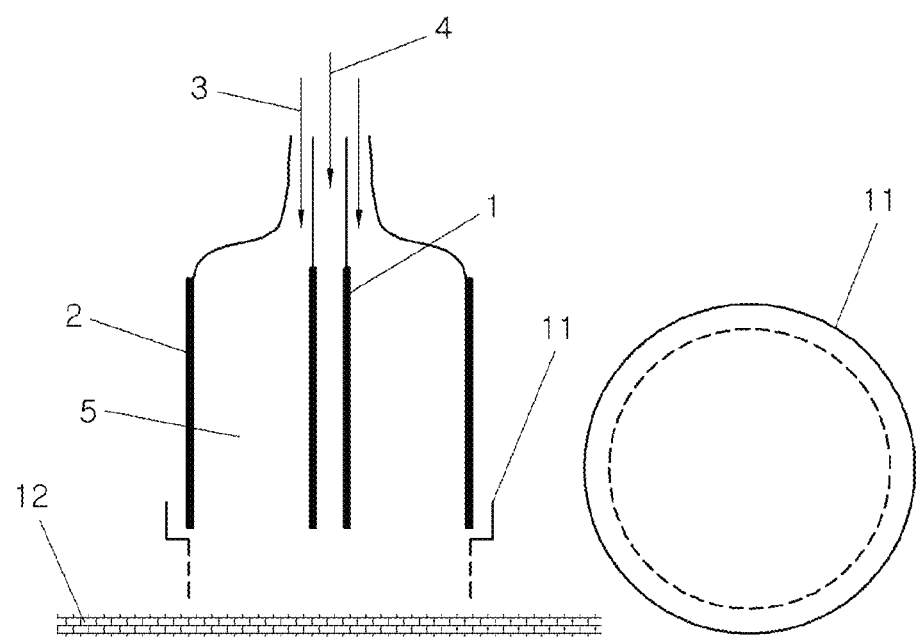
FIG. 11 schematically shows the reactive decontamination gas generator of FIG. 3 provided with a contact-proof ventilation guide.

FIG. 11 shows the reactive decontamination gas generator 30, which includes a hollow spacing panel 11 attached thereto. The hollow spacing panel 11 functions to prevent the interruption of the emission of the decontamination gas due to the contact of a spray outlet (60 in FIG. 1), through which, as the decontamination gas, a plasma gas and a reactive gas are sprayed, with the surface of the subject of decontamination, thereby facilitating the flow of the decontamination gas or air within the inside sealed by the enclosing cover. Furthermore, in order to prevent current leakage between the electrodes and the surface of the subject of decontamination, the hollow spacing panel functions to space the enclosing cover, having the reactive decontamination gas generator, apart from the surface of the subject of decontamination by a predetermined distance.

Figure 12:
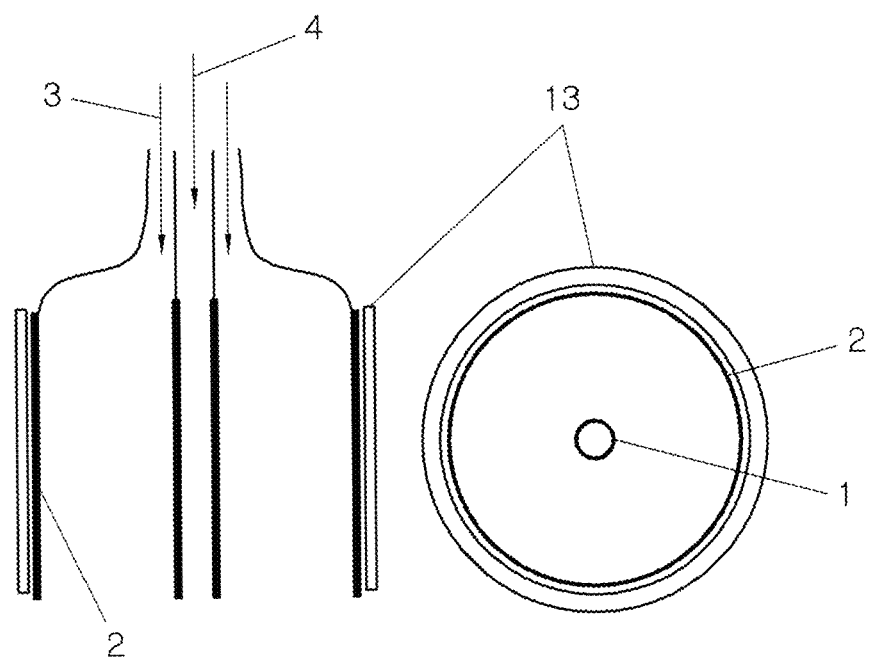
FIG. 12 schematically shows the reactive decontamination gas generator of FIG. 3, the outer surface of which is wrapped with an insulation material.

In the decontamination and sterilization device of the present invention, an insulation material 13 for preventing current leakage may be provided so as to wrap the outer surface of the external electrode, which is located at the outermost position of the reactive decontamination gas generator, as shown in FIG. 12.

The plasma generation efficiency, that is, the electron density, may vary depending on, the water content of the air or gas loaded in the space between the electrodes under an electric field for generating plasma by high voltage. This is because electric power may be consumed to decompose water or because the concentration of reactive material or radical such as ozone ($O_3$), .$O^-$, or $OH^-$ may vary while water decomposes. The water content of the air that is introduced into the plasma electrode has to be controlled in, consideration of the electric power or decomposition efficiency upon operation of the plasma electrode.

Figure 13:
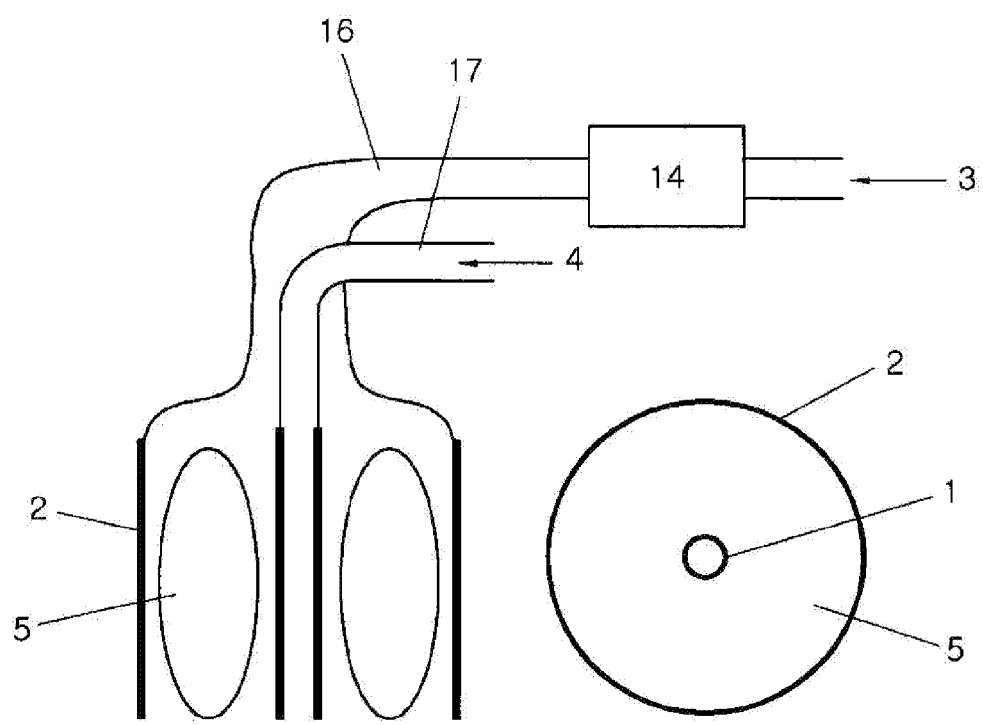
FIG. 13 schematically shows the reactive decontamination gas generator of FIG. 3 in which a humidity controller is provided at the reactive gas feed position.

Thus, as shown in FIG. 13, a humidity controller 14 for controlling relative humidity may be further provided to one side of the first inflow path 16, through which the external air is introduced to the reactive decontamination gas generator.

Although not shown, the enclosing cover may further include an air ventilation fan for circulating the air therein.

In addition, the decontamination and sterilization device of the invention as described above may be used as a structural unit for providing an expandable decontamination and sterilization device assembly in a manner such that individual structural units are repeatedly connected to each other using connectors formed at the edges of individual enclosing covers thereof. Such an expandable decontamination and sterilization device assembly is schematically illustrated in FIG. 14.

Here, any connector may be used without particular limitation, so long as it has a shape that enables the enclosing covers of the individual structural units to be removably connected to each other. The individual structural units may be removably attached to each other using a variety of connectors that may be easily used by those skilled in the art.

Figure 14:
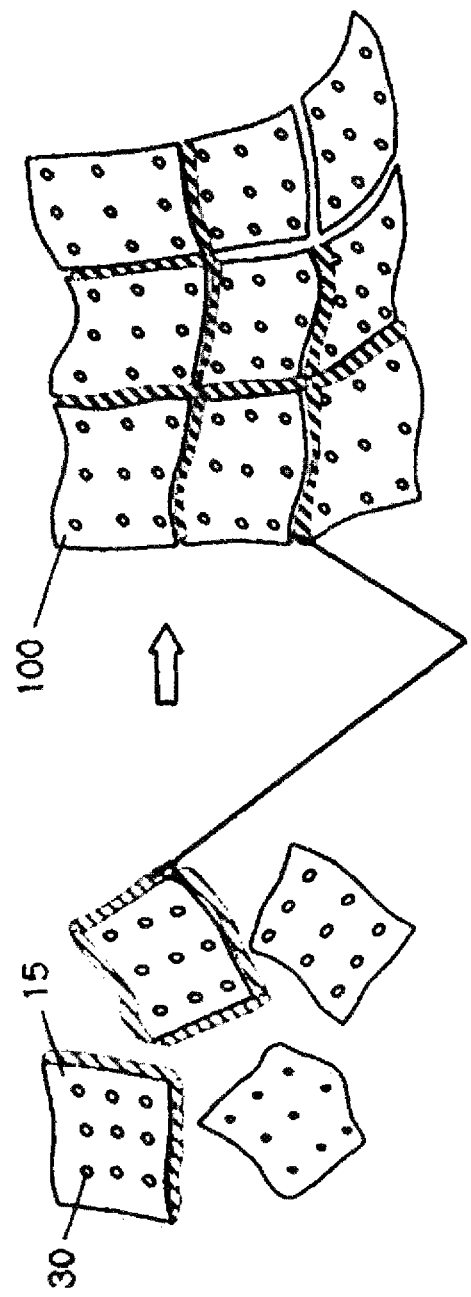
FIG. 14 schematically shows an expandable decontamination and sterilization device assembly, in which individual decontamination and sterilization devices are connected to each other using connectors according to an embodiment of the present invention.

In the expandable configuration of FIG. 14, the individual structural units are depicted as being separate from each other by a predetermined interval, which is however intended to understand the formation of an expandable decontamination and sterilization device assembly from the individual structural units. In real-world applications, the expandable decontamination and sterilization device assembly is configured such that individual decontamination and sterilization devices are not separated but are joined with each other by means of the connectors, as mentioned above.

Meanwhile, as for the decontamination and sterilization device of the invention, in order to evaluate the chemical agent decontamination performance of the decontamination gas comprising the plasma gas and the reactive gas, which are mixed, hydrogen peroxide ($H_2O$) vapor is used as the reactive gas, and the plasma electrode is designed to generate a dielectric barrier discharge (DBD).

Figure 15:
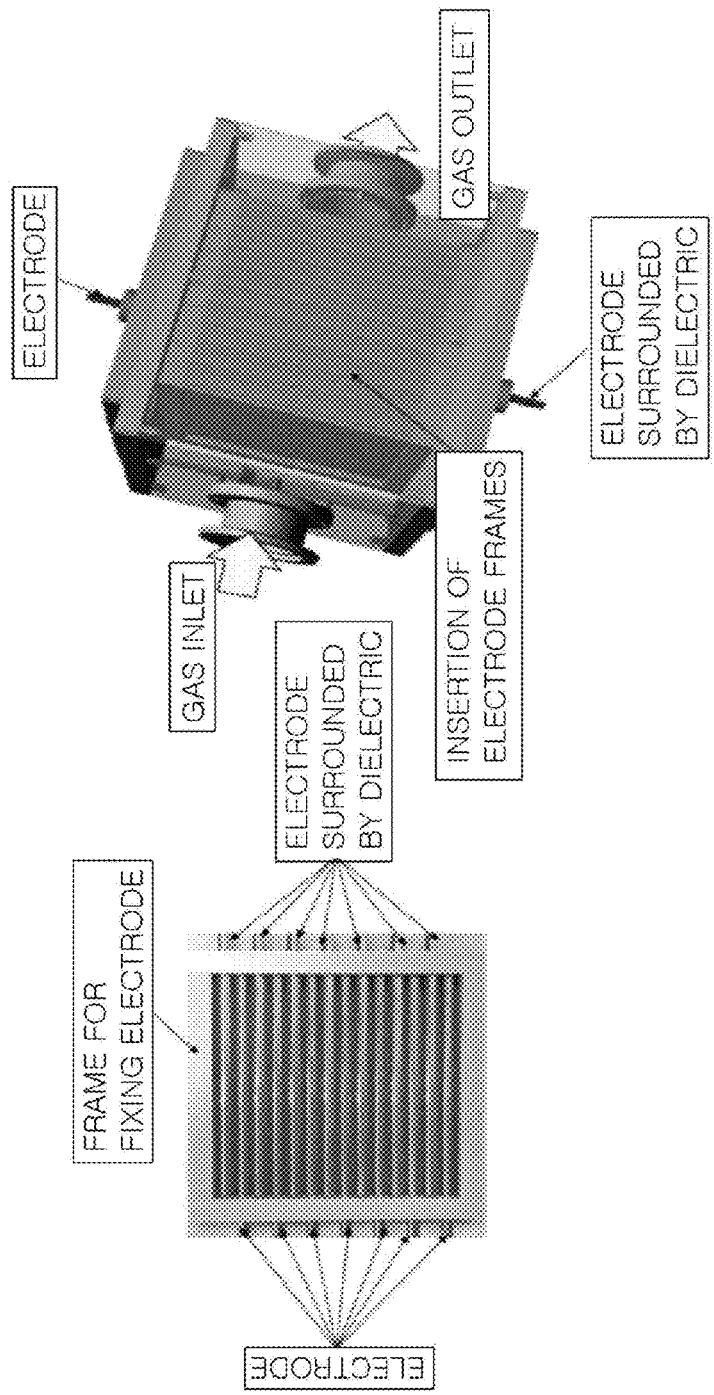
FIG. 15 shows the configuration of a rector used in the test of the present invention.

FIG. 15 shows the configuration of a reactor for evaluating decontamination performance. Specifically, 7 copper bar electrodes for applying high-voltage power and 7 electrodes surrounded by dielectric quartz tubes are spaced apart from each other by an interval of about 1 mm, and a total of 14 such electrodes is fixed to a frame having a size of about 150 mm×150 mm. A flow path is designed so that the decontamination gas comprising the plasma and the reactive gas, which are mixed, is introduced into a decontamination chamber through a filter-type decontamination reactor.

The inlet and the outlet of the plasma reactor are designed such that hydrogen peroxide vapor passes through the plasma reactor. As such, plasma is discharged between electrode-quartz-electrode using a power source for generating a low-frequency pulse of 20 kHz, 35% hydrogen peroxide is converted into 3 g of vapor per min, and the flow rate is fixed at 300 rpm.

During the decontamination, the concentration of hydrogen peroxide vapor is set to the range from 400 to 700 ppm. In a 1 $m^3$ sized decontamination space, a chemical agent resistant coating (CARC) sample contaminated with 1 $g/m^2$ of VX (methylphosphonothioic acid S[2-[bis(1-methylethyl)amino]ethyl]O-ethyl ester), which is a nerve agent, is decontaminated for 60 min. The inner temperature of the decontamination chamber is 28° C., and the inner humidity of the decontamination chamber is set to about 30%.

As is apparent from FIG. 16, the use of only hydrogen peroxide vapor or only plasma can be seen to decontaminate the VX nerve agent to similar levels. However, when the mixture of plasma and hydrogen peroxide is used, a 100% decontamination effect can be found to result most rapidly.

Hence, when using the mixture comprising the plasma gas and the reactive gas as the decontamination gas in the present invention, the reactive gas is decomposed and the resulting additional reactive radical, such as ozone ($O_3$), .$O^-$, or $OH^-$, is able to actively decompose the contaminants, thus increasing the decontamination and sterilization efficiency on the contaminated surface.

When the plasma gas including the radical produced from the reactive decontamination gas generator is introduced to the inside sealed by the enclosing cover, it may be mixed with the reactive gas such as hydrogen peroxide ($H_2O_2$), water ($H_2O$), or alcohol ($C_nH_{2n+1}OH$), thus realizing more efficient decontamination.

In particular, when the flexible enclosing cover is used, the reactive gas generated from the reactive decontamination gas generator is not diffused to the atmosphere but is intensively applied to the contaminated surface, and also, the conventional plasma gas is mixed with the safe reactive gas to thus increase the production of an active radical, thereby increasing decomposition efficiency through the contact reaction with the contaminants.

The aforementioned preferable embodiments are provided so that the present invention can be performed by those skilled in the art, and the above embodiments and the appended drawings are merely set forth to illustrate, but are not construed to limit the scope of the present invention. Accordingly, those skilled in the art will appreciate that various modifications, additions and substitutions are possible, without departing from the scope and spirit of the invention as disclosed in the accompanying claims.

What is claimed is:

1. A decontamination, and sterilization device comprising:
    an enclosing cover composed of a non-conductive flexible material and configured to cover and seal a portion of a surface of a subject of decontamination contaminated with a chemical weapon or a biological weapon, without coming into contact with the surface of the subject of decontamination; and
    a plurality of reactive decontamination gas generators spaced apart from each other by a predetermined distance and attached on the surface of the enclosing cover and configured such that a plasma gas and a reactive gas for producing an active radical are simultaneously or independently sprayed to an inside sealed by the enclosing cover via a spray outlet of each of the reactive decontamination gas generators,
    wherein each of the reactive decontamination gas generators includes an electrode structure which includes at least one internal electrode and at least one external electrode and is configured such that the at least one internal electrode receives external air via a first inflow path formed at one end thereof to generate plasma and is housed in the at least one external electrode, and
    wherein the enclosing cover is used as a structural unit such that individual structural units are connected to each other using connectors formed at edges of individual enclosing covers thereof.

2. The decontamination and sterilization device of claim 1, wherein the at least one internal electrode communicates with a second inflow path through which the reactive gas flows, so that the reactive gas is fed into the at least one internal electrode.

3. The decontamination and sterilization device of claim 2, wherein the at least one internal electrode is provided in a form of a tube having a cylindrical shape or a tetragonal prismatic shape.

4. The decontamination and sterilization device of claim 1, wherein the at least one external electrode is configured to include a dielectric formed around an inner surface of the at least one external electrode so as to come into contact therewith.

5. The decontamination and sterilization device of claim 1, wherein a dielectric material is provided between the at least one internal electrode and the at least one external electrode and includes at least one selected from among $BaTiO_3$, $TiO_2$, glass, and ceramic.

6. The decontamination and sterilization device of claim 1, wherein the electrode structure is configured such that a plurality of internal electrodes and a plurality of external electrodes are alternately arranged, wherein each of the internal electrodes is of a metal tube-type.

7. The decontamination and sterilization device of claim 1, wherein the electrode structure is configured to include an insulation material formed around an outer surface of an external electrode located at an outermost position in order to prevent current leakage.

8. The decontamination and sterilization device of claim 1, wherein needle-shaped electrodes are formed at a position in which the at least one internal electrode and the at least one external electrode are disposed to face each other.

9. The decontamination and sterilization device of claim 1, wherein the enclosing cover includes an opening/closing-type fixing jig for fixing each of the reactive decontamination gas generators, and the fixing jig enables one end of the reactive decontamination gas generator to be removably attached to the enclosing cover in a screw-fastening manner or a one-touch coupling manner.

10. The decontamination and sterilization device of claim 1, wherein each of the reactive decontamination gas generators includes a hollow spacing panel attached thereto so as to prevent the spray outlet from coming into contact with the surface of the subject of decontamination.

11. The decontamination and sterilization device of claim 1, wherein the first inflow path includes a humidity controller for controlling a relative humidity of external air that is introduced into each of the reactive decontamination gas generators.

12. The decontamination and sterilization device of claim 1, wherein the enclosing cover includes an air ventilation fan for circulating air therein.

13. The decontamination and sterilization device of claim 1, wherein the enclosing cover further includes a fixing member at an edge thereof so as to prevent blowing thereof due to a wind, whereby the enclosing cover is fixed to or is kept in close contact with the surface of the subject of decontamination.

14. The decontamination and sterilization device of claim 1, wherein the reactive gas includes at least one selected from among hydrogen peroxide ($H_2O_2$), water vapor ($H_2O$), helium, argon, acetone, oxygen, compressive air, and alcohol ($C_nH_{2n+1}OH$).

* * * * *